(12) United States Patent
Ohmuraya et al.

(10) Patent No.: US 10,010,059 B2
(45) Date of Patent: Jul. 3, 2018

(54) METHOD FOR PRODUCING MODEL ANIMAL, AND MODEL ANIMAL

(75) Inventors: Masaki Ohmuraya, Kumamoto (JP); Kimi Araki, Kumamoto (JP)

(73) Assignee: NATIONAL UNIVERSITY CORPORATION KUMAMOTO UNIVERSITY, Kumamoto-Shi (JP)

( * ) Notice: Subject to any disclaimer, the term of this patent is extended or adjusted under 35 U.S.C. 154(b) by 1038 days.

(21) Appl. No.: 14/355,432

(22) PCT Filed: Jun. 19, 2012

(86) PCT No.: PCT/JP2012/065668
§ 371 (c)(1),
(2), (4) Date: Apr. 30, 2014

(87) PCT Pub. No.: WO2013/094240
PCT Pub. Date: Jun. 27, 2013

(65) Prior Publication Data
US 2014/0289878 A1 Sep. 25, 2014

(30) Foreign Application Priority Data

Dec. 22, 2011 (JP) .................................. 2011-282413

(51) Int. Cl.
| | |
|---|---|
| A01K 67/00 | (2006.01) |
| A01K 67/033 | (2006.01) |
| C12N 15/00 | (2006.01) |
| A01K 67/027 | (2006.01) |
| C12N 15/873 | (2010.01) |
| C12N 15/85 | (2006.01) |
| C12N 5/0735 | (2010.01) |

(52) U.S. Cl.
CPC ...... *A01K 67/0276* (2013.01); *A01K 67/0271* (2013.01); *C12N 5/0606* (2013.01); *C12N 15/8509* (2013.01); *C12N 15/873* (2013.01); *A01K 2217/05* (2013.01); *A01K 2227/105* (2013.01); *A01K 2267/03* (2013.01)

(58) Field of Classification Search
CPC .................. A01K 67/0276; A01K 67/0278
See application file for complete search history.

(56) References Cited

U.S. PATENT DOCUMENTS

2010/0279923 A1  11/2010  Schulte et al.

FOREIGN PATENT DOCUMENTS

| JP | 2008-67696 A | 3/2008 |
| WO | WO 2008/098720 A1 | 8/2008 |

OTHER PUBLICATIONS

Jacob (Trends in Genetics, 2010, 26:510-518).*
Cao et al. (J. of Exp. Zoo., 311A: 368-376, 2009).*
Brevini et al. (Theriogenology, 74: 544-550, 2010).*
Paris et al.(Theriogenology, 74: 516-524, 2010).*
Ohmuraya (Jun. 25, 2011, Pancreatic Research Abstracts, 23(3):326, listed on IDS filed Apr. 30, 2014, ref. 11; English Translation.*
Guan (2010, Genesis, 48:73-85).*
Cox et al., "Phenotypic annotation of the mouse X chromosome," Genome Research, vol. 20, No. 8, (Supplemental Table 2), Aug. 2010, pp. 1154-1164.
The Association for Research of Vision and Ophthalmology. "Investigative Opthalmology & Visual Science, Abstract Book," vol. 37, No. 3, Feb. 15, 1996, p. S699 (2 pages total).
Archer et al., "A Mouse Model of Hereditary Pancreatitis Generated by Transgenic Expression of R122H Trypsinogen", Gastroenterology, 2006, vol. 131, pp. 1844-1855.
International Search Report for PCT/JP2012/065668 dated Sep. 25, 2012.
Jacobs et al., "Emergence of Novel Color Vision in Mice Engineered to Express a Human Cone Photopigment", Science, 2007, vol. 315, No. 5819, pp. 1723-1725.
Morey et al., "Genetics and epigenetics of the X chromosome", Annals of the New York Academy of Sciences, The Year in Human and Medical, 2011, vol. 1214, pp. E18-E33.
Ohmuraya et al., "Autophagic Cell Death of Pancreatic Acinar Cells in Serine Protease Inhibitor Kazal Type 3-Deficient Mice", Gastroenterology, Aug. 2005, vol. 129, No. 2, pp. 696-705.
Ohmuraya et al., "The Roles of Serine Protease Inhibitor Kazal Type 1 (SPINK1) in Pancreatic Diseases", Experimental Animals, 2011, vol. 60, No. 5, pp. 433-444.
Omuraya et al., "Sui Kiso Kenkyu no Atarashii Choryu—Bench to Bed o Mezashite—Suien ni Okeru Autophagy no Igi", Journal of Biliary Tract & Pancreas, 2010, vol. 31, No. 6, pp. 559-564.
Omuraya et al., "X Senshokutai Fukasseika ni yoru Idenshi Kaihen Mansei Suien Model Mouse no Juritsu", The Journal of Japan Pancreas Society, Jun. 25, 2011, vol. 26, No. 3, W2-3, p. 326.
Onishi et al., "Generation of Knock-in Mice Carrying Third Cones with Spectral Sensitivity Different from S and L Cones", Zoological Science, 2005, vol. 22, pp. 1145-1156.

* cited by examiner

*Primary Examiner* — Valarie E Bertoglio
(74) *Attorney, Agent, or Firm* — Birch, Stewart, Kolasch & Birch, LLP

(57) ABSTRACT

A method for producing a model animal which has a desired lifetime, and in which a predetermined biological reaction can be induced, and a model animal are provided. The present invention produces a first individual in which a gene of interest is heterozygously deficient using a first ES cell from a non-human mammalian animal. Meanwhile, a fragment containing a homologous gene that has homology to the gene of interest is made, a second ES cell constituted so that a predetermined region on X chromosome of the animal can be substituted is used, and the fragment is introduced into the second ES cell to generate a substituted ES cell in which the predetermined region has been substituted with the fragment. A second individual is produced using the substituted ES cell. The first individual and the second individual are mated with each other to produce a model animal.

3 Claims, 16 Drawing Sheets

F I G. 1
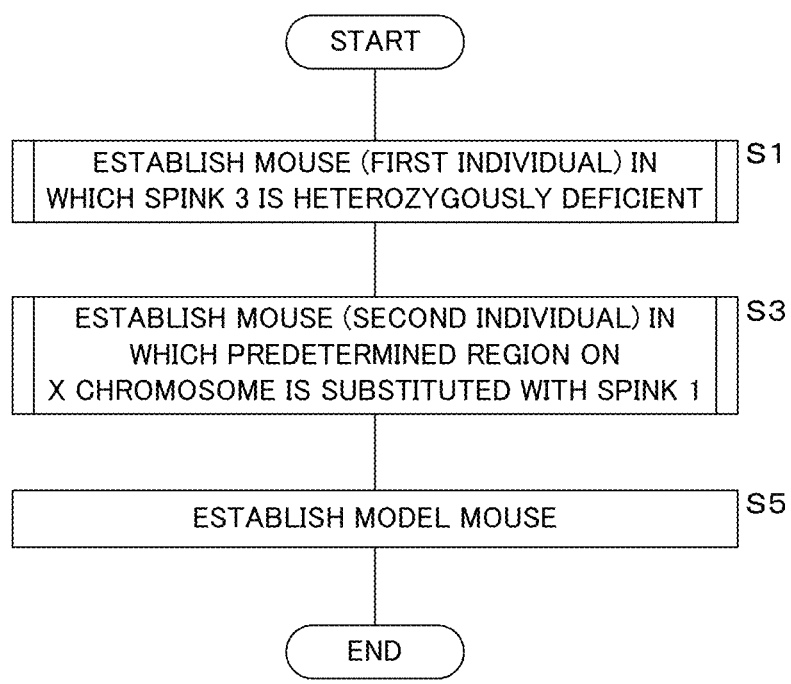

F I G. 8
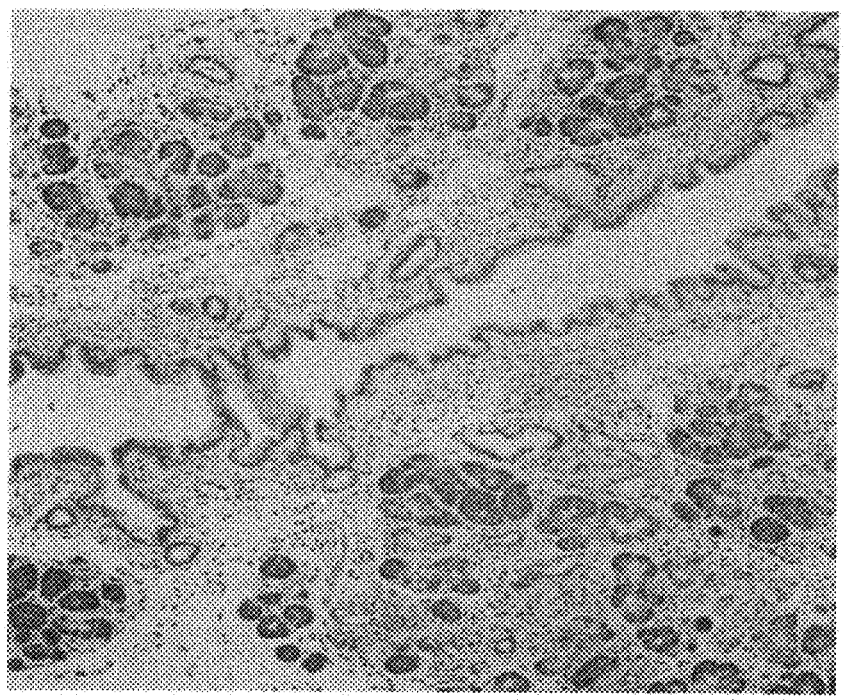

F I G. 9
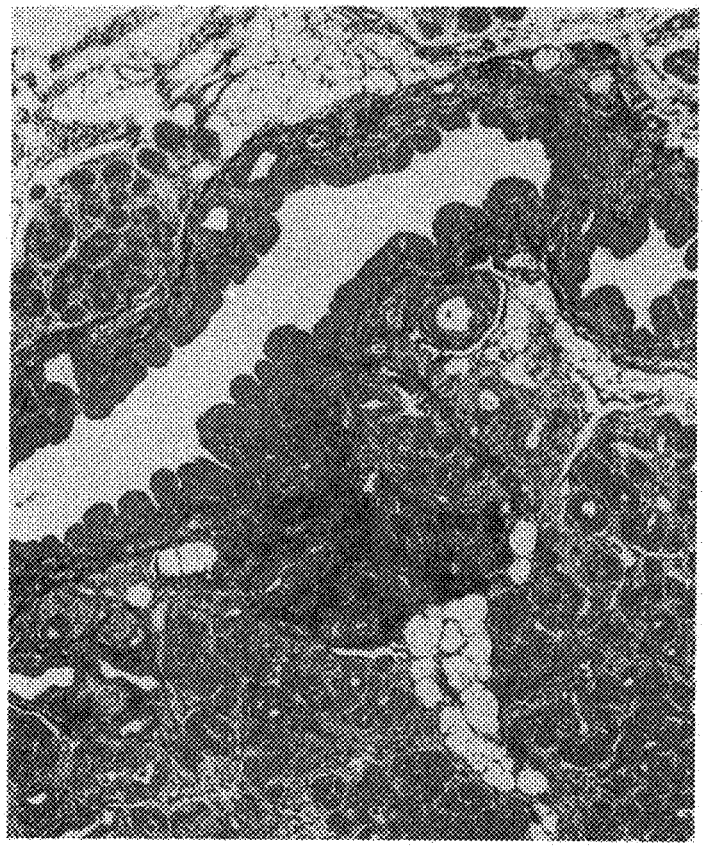

F I G. 1 1
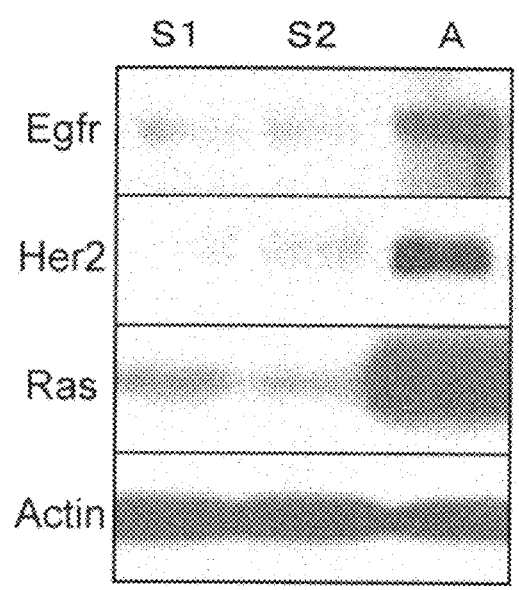

F I G. 1 3
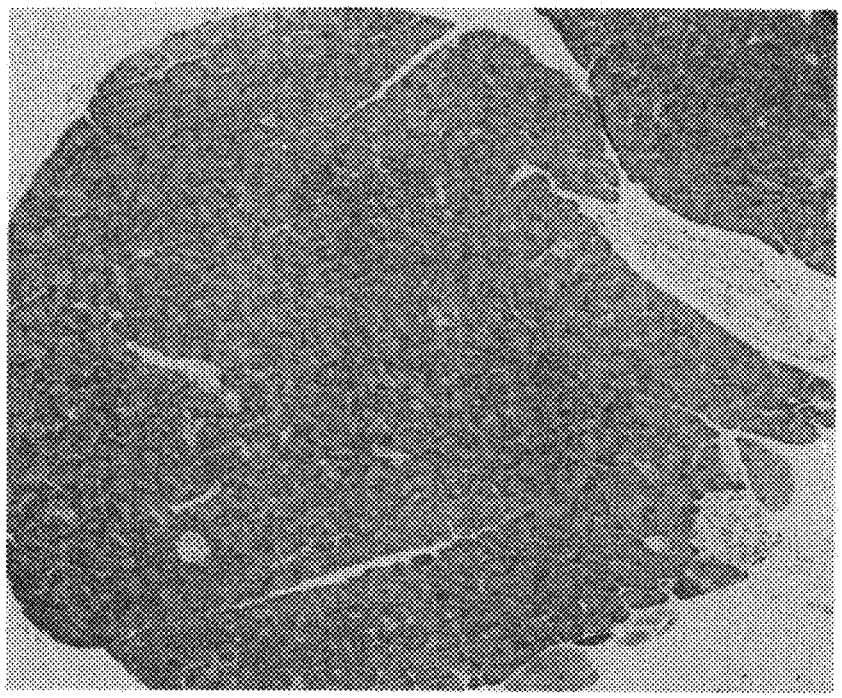

F I G. 1 4

F I G. 16
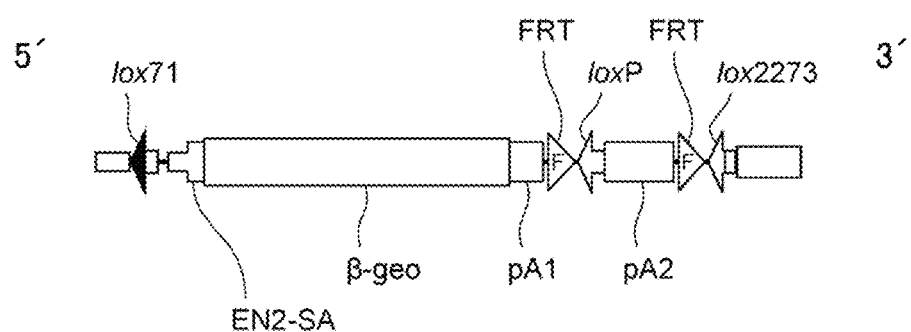

METHOD FOR PRODUCING MODEL ANIMAL, AND MODEL ANIMAL

CROSS-REFERENCE TO RELATED APPLICATIONS

This non-provisional application is a National Stage entry under U.S.C. § 371 of International Application No. PCT/JP2012/065668 filed on Jun. 19, 2012, which claims priority to Japanese Patent Application No. 2011-282413 filed in Japan on Dec. 22, 2011. The entire contents of all of the above applications are hereby incorporated by reference.

FIELD

The present invention relates to a method for producing a non-human mammalian model animal by modifying genes, and a model animal produced by the method.

BACKGROUND

It has been desired to develop an effective therapy for diseases with chronic pancreatitis, and it is efficient in a development process for such a therapy to use a model animal that develops chronic pancreatitis.

Pancreatitis is thought to be caused by unbalance between an activity of trypsin produced in pancreas and an activity of an inhibitor that inhibits the activity of the trypsin.

That is, when the activity of the trypsin is relatively higher than the activity of the inhibitor or when the activity of the inhibitor is relatively lower than the activity of the trypsin, the pancreatitis is caused.

Thus, as a model animal that develops the pancreatitis, a model animal modified to express excessively tripsinogen has been produced by injecting a transcription gene constructed using fragments each encoding an esterase promoter as well as a polyadenylation site of pancreatic tripsinogen, β-globin and an SV40 from a wild mouse into a pronucleus of a C57B1/6 mouse fertilized egg (see Herbert Archer et al., A mouse model of hereditary pancreatitis generated by transgenic expression of R122H tripsinogen, Gastroenterology, 2006, Vol. 131, p 1844-1855).

However, the model mouse produced by such conventional methods was problematic in that loss of pancreatic gland cells and fibrosis of pancreas which were characteristic observations for human chronic pancreatitis were not observed. That is, no model mouse for the chronic pancreatitis can be produced by the aforementioned conventional method.

Thus the present inventors produced knockout mice in which a Spink 3 (serine protease inhibitor Kazal type 3) gene that is a mouse homolog for human Spink 1 (serine protease inhibitor Kazal type 1) had been knocked out (see Masaki Ohmuraya et al., Autophagic cell death of pancreatic acinar cell in serine protease inhibitor Kazal type 3-deficient mice, Gastroenterology, 2005, Vol. 129, p 696-705)

SUMMARY

However, the produced knockout mice caused cell death in all acinar cells immediately after birth, thereby causing exocrine dysfunction resulting in death in two weeks after birth.

The present invention has been made in the light of such a circumstance, and provides a method for producing a model animal which has a desired lifetime and in which a predetermined biological reaction such as observations characteristic for human chronic pancreatitis can be induced, as well as the model animal produced by the method.

The method for producing the model animal according to the present invention is characterized in that when a model animal in which a gene of interest is deficient is produced using an ES cell from a non-human mammalian animal, a first individual in which the gene of interest is heterozygously deficient is obtained, and is characterized by performing a step of making a fragment containing a homologous gene of the gene of interest, a step of using a second ES cell constituted so that a predetermined region of X-chromosome of the non-human mammalian mammal can be substituted to generate a substituted ES cell in which the predetermined region is substituted with the fragment by introducing the fragment into the second ES cell and a step of producing a second individual using the obtained substituted ES cell, and by producing the model animal by mating the first individual and the second individual with each other.

In the method for producing the model animal of the present invention, the first individual in which the gene of interest is heterozygously deficient is obtained by the standard method.

On the other hand, the fragment containing the homologous gene that has homology to the aforementioned gene of interest is made. In such a step, the homologous gene may be cloned or a gene sequence designed to contain each exon composing the homologous gene may be synthesized. Then, the substituted ES cell in which the predetermined region has been substituted with the fragment containing the homologous gene is generated by introducing the fragment together with an expression vector such as Cre expression vector into the second ES cell constituted so that the predetermined region on the X chromosome of the animal can be substituted. Subsequently, the obtained substituted ES cell is treated appropriately, and then transferred into a pseudopregnant animal to produce individuals. A second individual in which the predetermined region on the X chromosome has been substituted with the homologous gene is selected from the obtained individuals.

The first individual and the second individual are mated with each other to produce a female model animal in which the gene of interest has been homozygously deficient and the homologous gene can be expressed on one of the paired X chromosomes.

Here, gene dosage compensation in the mammalian animal is accomplished by inactivating one of two X chromosomes in the female, and such a phenomenon is referred to as "X chromosome inactivation". Any one of the two X chromosomes is randomly inactivated. Thus, in the model animal produced as above, cells in which the gene of interest is deficient but the deficiency is rescued by the homologous gene on the X chromosome and cells in which the gene of interest is deficient and such a rescue is not made randomly compose a target part. Such a model animal has the desired lifetime and induces the predetermined biological reaction.

The method for producing the model animal according to the present invention is also characterized by, when producing a model animal in which a gene of interest is deficient using an ES cell from a non-human mammalian animal, performing a step of deleting the gene of interest using a first ES cell from the non-human mammalian animal and a step of producing a first individual in which the gene of interest is heterozygously deficient using the obtained first ES cell, while performing a step of making a fragment containing a homologous gene that has the homology to the gene of interest, a step of using a second ES cell constituted so that a predetermined region on X chromosome of the non-human mammalian animal can be substituted to generate a substituted ES cell in which the predetermined region is substituted with the fragment by introducing the fragment into the second ES cell and a step of producing a second individual using the obtained substituted ES cell, and by mating the first individual and the second individual with each other.

In the method for producing the model animal of the present invention, a targeting vector corresponding to the gene of interest is made, and the first ES cell in which the gene of interest is deficient is obtained by introducing the targeting vector into the first ES cell from the non-human mammalian animal. Then, the obtained first ES cell is appropriately treated, subsequently transferred into a pseudopregnant animal to produce individuals, and the first individual in which the gene of interest is heterozygously deficient is selected from the obtained individuals. This can certainly yield the first individual in which the desired gene of interest has been heterozygously deficient.

Meanwhile, like above, the fragment containing the homologous gene that has the homology to the gene of interest is made. The substituted ES cell in which the predetermined region has been substituted with the fragment is generated by introducing the fragment into the second ES cell constituted so that the predetermined region on the X chromosome of the animal ran be substituted. The obtained substituted ES cell is appropriately treated, subsequently transferred into the pseudopregnant animal to produce the individuals, and the second individual in which the predetermined region on the X chromosome has been substituted with the homologous gene is selected from the obtained individuals.

And, the first individual and the second individual are mated with each other, thereby producing the female model animal in which the gene of interest is homozygously deficient and the homologous gene can be expressed on one of the paired X chromosomes. This can yield the model animal which has the desired lifetime and in which the predetermined biological reaction is induced, like above.

The method for producing the model animal according to the present invention is also characterized by using the ES cell constituted so that the predetermined region on one X chromosome of the paired X chromosomes can be substituted, as the second ES cell.

The second ES cell constituted so that the predetermined region on the X chromosome can be substituted by introducing an appropriate vector into the one X chromosome of the paired X chromosomes is used in the method for producing the model animal of the present invention. At that time a position of the X chromosome to which another gene is introduced should have no influence on ecology of the model animal derived from the second ES cell. By virtue of this, the objective model animal can be obtained efficiently and certainly by applying the aforementioned X chromosome inactivation.

The method for producing the model animal of the present invention is characterized by using a mouse as the non-human mammalian animal and using an ES cell in which the predetermined region is provided in a Diap 2 gene region on the X chromosome as the second ES cell.

The Diap 2 gene is located on the X chromosome, and it has been confirmed that mice in which the Diap 2 gene is deficient are normal. Therefore, when the ES cell in which the predetermined region is provided in the Diap 2 gene region on the X chromosome is used as the second ES cell, the predetermined biological reaction can be induced without giving the harmful effect to the obtained model mouse.

The method for producing the model animal according to the present invention is characterized by using an ES cell (NITE BP-1172) as the second ES cell.

The ES cell (NITE BP-1172) is used as the second ES cell in the method for producing the model animal of the present invention. This second ES cell was domestically deposited to Incorporated Administrative Agency, National Institute of Technology and Evaluation (NITE), Patent Microorganisms Depositary (NPMD) (2-5-8 Kazusa Kamatari, Kisarazu-shi, Chiba Prefecture, Japan, 292-0818) on Dec. 1, 2011 (original deposit date), and an accession number of NITE P-1172 has been given. Further, this ES cell was transferred to the international depositary of the Patent Microorganisms Depositary on May 30, 2012 (transfer date), and the accession number of NITE BP-1172 has been given on Jun. 11, 2012.

This second ES cell (NITE BP-1172) is constructed by introducing pU-21B that is a trap vector into the aforementioned Diap 2 gene, and a predetermined region of the trap vector pU-21B can be substituted with another fragment. Therefore, the homologous gene can be introduced into the Diap 2 gene by substituting this substitutable region with the fragment containing the homologous gene. Meanwhile, the mouse in which the Diap 2 gene is deficient is normal as described above. Thus, when the ES cell (NITE BP-1172) is used as the second ES cell, the predetermined biological reaction can be induced without giving the harmful effect to the obtained model mouse.

The method for producing the model animal according to the present invention is characterized in that the gene of interest is a Spink 3 gene and the homologous gene is a Spink 1 gene.

In the method for producing the model animal of the present invention, the observations characteristic for human chronic pancreatitis can be observed in the obtained model mouse because the gene of interest is the Spink 3 gene and the homologous gene is the Spink 1 gene.

The model animal according to the present invention is a non-human mammalian animal, and is characterized by being a female in which a gene of interest is homozygously deficient, the fragment containing a homologous gene that has homology to the gene of interest has been introduced into X chromosome and the homologous gene is expressed in some cells of cells composing a body.

In the model animal of the present invention, the gene of interest is homozygously deficient, thus when the gene of interest is required to support life, the life of the model animal cannot be supported if this goes on. Thus, the homologous gene that has the homology to the gene of interest is knocked in the chromosome of the model animal. However, when the homologous gene is simply knocked in, the deficiency of the gene of interest is only rescued. Thus, when the gene of interest is associated with the disease, the model animal does not develop such a disease and the normal model animal is obtained simply.

Thus, in the present invention, the homologous gene can be expressed by introducing the fragment containing the homologous gene that has the homology to the gene of interest into the X chromosome of the model animal.

Due to the aforementioned X chromosome inactivation, the homologous gene is expressed in some cells of the cells composing the body of the model animal and the homologous gene is not expressed in the other cells thereof. That is, the cells in which the gene of interest is homozygously deficient but its deficiency is rescued by the homologous gene on the X chromosome and the cells in which the gene of interest is homozygously deficient and such a rescue is not made are present mixedly and randomly. Due to this phenomenon, this model animal has the desired lifetime while induces the biological reaction such as the predetermined disease.

The model animal according to the present invention is a non-human mammalian animal and is characterized by being a female which is produced by mating a first individual in which a gene of interest has been heterozygously deficient with a second individual in which a fragment containing a homologous gene that has homology to the gene of interest has been introduced into the X chromosome of the non-human mammalian animal, and in which the gene of interest is homozygously deficient and the homologous gene is expressed in some cells of cells composing a body.

The model animal of the present invention is the non-human mammalian animal and is produced by mating the first individual in which the gene of interest is heterozygously deficient with the second individual in which the fragment containing the homologous gene that has the homology to the gene of interest is introduced into the X chromosome of the animal. The first individual and the second individual can stably conserve the traits, and thus, the traits of the model animal of the present invention are also stable.

The model animal is the female in which the gene of interest is homozygously deficient and the homologous gene introduced into the X chromosome as described above is expressed in some cells of the cells composing the body. Thus, like above, the model animal has the desired lifetime while induces the biological reaction such as the predetermined disease.

The model animal according to the present invention is characterized in that the fragment has been introduced into a Diap 2 gene region on the X chromosome.

In the model animal of the present invention, the fragment is introduced into the Diap 2 gene region on the X chromosome, and thus the predetermined biological reaction can be induced like above without giving the harmful effect to the model animal.

The model animal according to the present invention is characterized in that the non-human mammalian animal is a mouse, the gene of interest is a Spink 3 gene and the homologous gene is a Spink 1 gene.

In the model animal of the present invention, the non-human mammalian animal is the mouse, the gene of interest is the Spink 3 gene and the homologous gene is the Spink 1 gene. Thus, the observations characteristic for human chronic pancreatitis can be observed like above in the obtained model mouse.

The above and further objects and features will more fully be apparent from the following detailed description with accompanying drawings.

BRIEF DESCRIPTION OF THE DRAWINGS

FIG. 1 is a flowchart illustrating a procedure for producing a model animal according to the present invention.

FIG. 8 is a microscopic image view of a pancreatic slice from a Spink $3^{-/-}$XCAG-SP1/wild mouse aged 8 weeks produced by the method of the present invention.

FIG. 9 is a microscopic image view showing a result of Azan staining of a pancreatic slice from a Spink $3^{-/-}$XCAG-SP1/wild mouse aged 8 weeks produced by the method of the present invention.

FIG. 11 is an image view showing a result of examining the presence or absence of expression of various markers by the western blotting method.

FIG. 13 is a microscopic image view of a pancreatic slice from a mouse aged 8 weeks in which Spink 3 was heterozygously deficient (Spink $3^{+/-}$).

FIG. 14 is a microscopic image view showing a result of Azan staining of a pancreatic slice from a mouse aged 8 weeks in which Spink 3 was heterozygously deficient (Spink $3^{+/-}$).

FIG. 16 is a schematic view illustrating a structure of pU-21B after being introduced into a Diap 2 gene region.

DETAILED DESCRIPTION

The present invention will be described in detail with reference to the drawings. The present invention is not limited to embodiments described later. Various modified aspects are included in the present invention in the range in which those skilled in the art can easily think of without departing from the description in claims.

Figure 2:
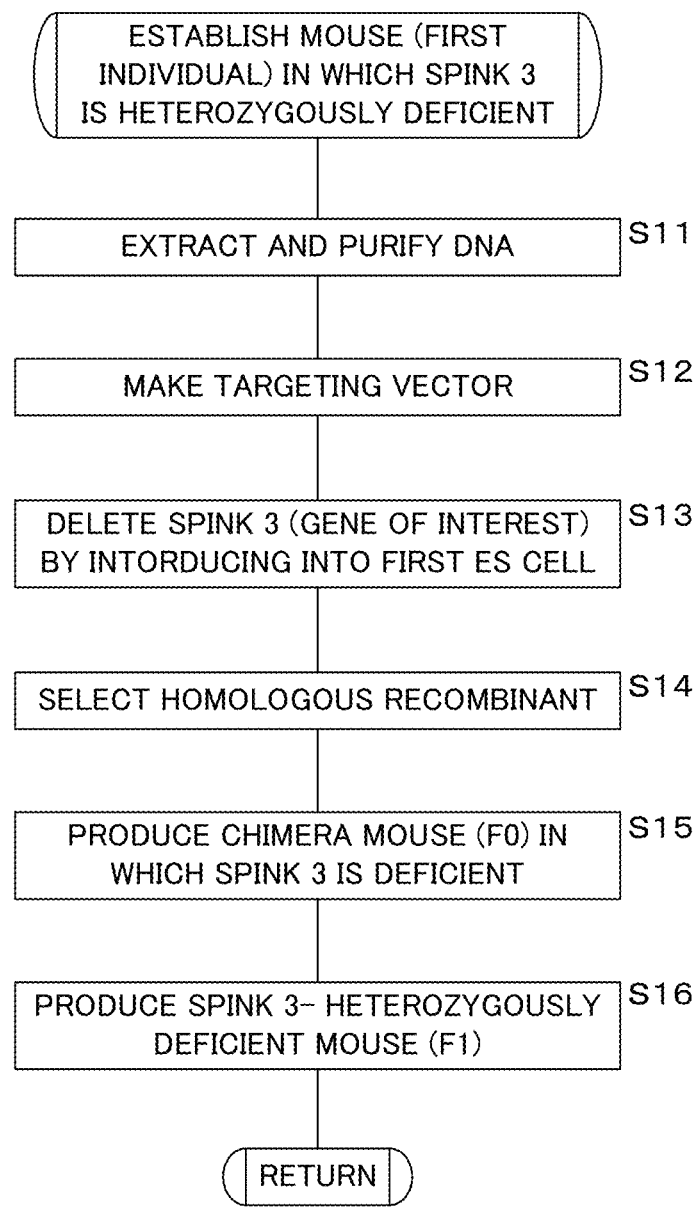
FIG. 2 is a flowchart illustrating a procedure for producing a model animal according to the present invention.
Figure 3:
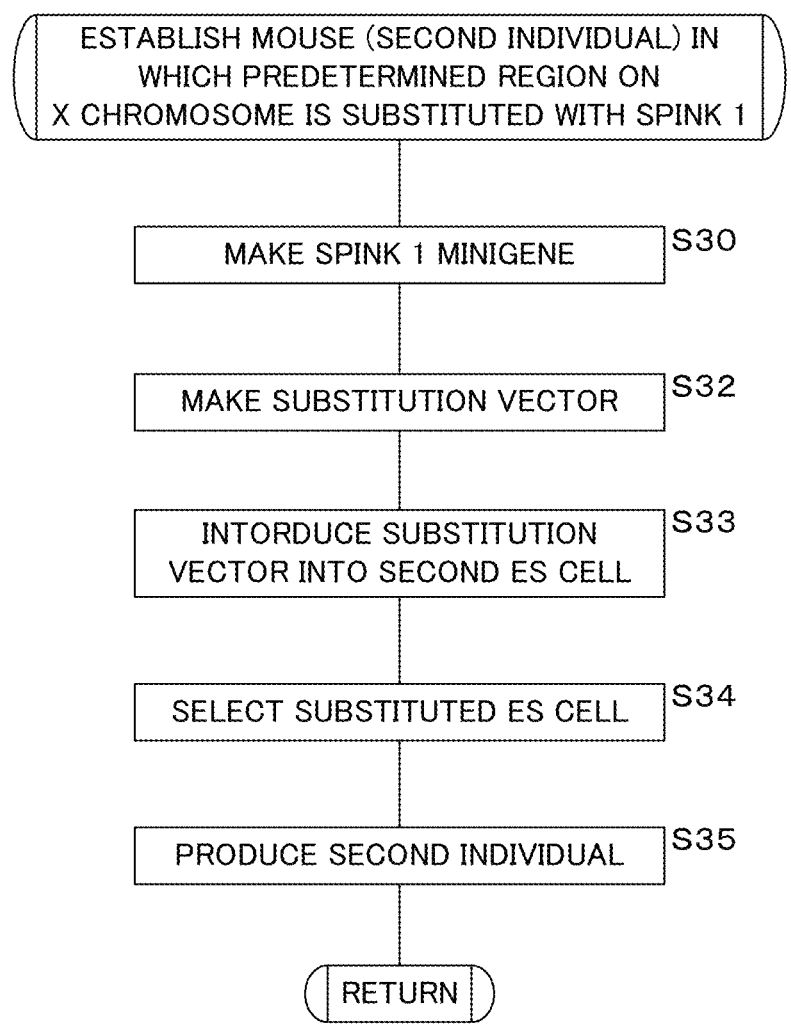
FIG. 3 is a flowchart illustrating a procedure for producing a model animal according to the present invention.

FIG. 1 to FIG. 3 are flowcharts illustrating the procedure for producing the model animal according to the present invention, and show cases applied to the production of the model mouse that develops chronic pancreatitis.

[Establishment of Mouse in which Spink 3 is Heterozygously Deficient] (Step S1)

As shown in FIG. 2, an appropriate part, preferably kidney is collected from an inbred strain C57BL/6J mouse (produced by CREA Japan Inc.), and DNA contained in cells in the part is extracted and purified (step S11).

DNA can be extracted and purified as follows. It is indisputable that the present invention is not limited to such exemplifications, and any methods can be applied as long as the desired object can be accomplished. The same shall apply hereinafter.

That is, the collected part is minced and an appropriate amount thereof is placed in a microtube. Then, 600 µl of lysis buffer (1×SSC, 1 mM EDTA, 20 mM Tris HCl buffer (pH 7.5)) and 80 µl of 10% (mass/volume) SDS solution are added to this microtube, the mixture is reacted at 55° C. for 2 to 3 hours with stirring with appropriate intervals, subsequently 0.5 to 1 µl of protein kinase K (20 mg/ml) is added thereto, and stirred and reacted for additional about one hour to lyse the cells in the microtube.

Then, a phenol/chloroform mixed solution is added in the same amount as the liquid in the microtube, the mixture is stirred thoroughly on a vortex and centrifuged at 12,000 to 15,000 rpm, and an upper layer that is an organic solvent layer is removed. After repeating the same manipulation, isopropyl alcohol is added in the same amount as the liquid in the microtube, and the mixture is stirred thoroughly until lint-like DNA is precipitated.

The mixture is centrifuged at a rotation frequency suitable for precipitating the lint-like DNA, and a supernatant is discarded. DNA is washed sequentially with 70% (volume/volume) ethanol and then 100% ethanol, and the supernatant after the centrifugation is discarded. This manipulation is repeated to evaporate and remove remaining ethanol. About 50 μl of an appropriate buffer such as Tris/EDTA buffer is added to DNA thus obtained and DNA is dissolved to obtain a DNA solution to be used as a template.

The DNA solution from the mouse is thus prepared. Subsequently, a targeting vector for producing a knockout mouse in which a Spink 3 gene is deleted is made as follows (step S12).

Here, the Spink 3 gene is composed of four exons of exon 1 to exon 4 as is the case with a Spink 1 gene. Thus, an appropriate region on a 5' side and an appropriate region on a 3' side that were homologous regions of the exon 1 were cloned. The appropriate region on the 5' side and the appropriate region on the 3' side may be designed to become about 10 kb in total.

Such a cloning can be performed as follows.

That is, a 2.2 kb region on the 5' side and a 8 kb region on the 3' side in the exon 1 of the Spink 3 gene were amplified, respectively by PCR using the following primers in advance designed desirably. PCR was performed by reacting at 94° C. for 5 minutes, then repeating 40 cycles of reactions at 90° C. for 20 seconds, 60° C. for 30 seconds and 68° C. for 3 minutes and finally reacting at 68° C. for 7 minutes using a PCR apparatus Gene Amp PCR System 9700 (manufactured by Applied Biosystems) and DNA polymerase (manufactured by Takara Bio Inc.).

```
                                          (SEQ ID NO: 1)
mPSTI-13:      5'-TACGTCTCCGGTCTTCTTCT-3'

(SEQ ID NO: 2)
loxP-B:        5'-GATCCGGAACCCTTAATATAA-3'
```

The resulting amplified fragment was purified using Maxiprep (manufactured by Qiagen) that was a purification kit, and subsequently the targeting vector was obtained by ligating the fragments to obtain a sequence, for example, (2.2 kb on the 5' side in the exon 1 of Spink 3)-(mutant lox)-(PGK promoter)-(neo cassette)-(mutant lox)-(8 kb on the 3' side in the exon 1 of Spink 3). The sequence (mutant lox)-(PGK promoter)-(neo cassette)-(mutant lox) was designed to be inserted into a restriction enzyme BglII site just before ATG that was an initiation codon in the exon 1 of the Spink 3 gene.

The PGK promoter that is a eukaryotic cell promoter and the neo cassette including a neomycin resistant gene are available from, for example, Kumamoto University, Institute of Resource Development and Analysis.

The mutant lox can be made by performing PCR using a primer obtained by adding about 5 b to a portion containing the mutation and a T3 or T7 primer outside of loxP, and subcloning the obtained fragment.

Meanwhile, the mutant lox can be made by synthesizing the following sequences.

```
Lox71:
                                          (SEQ ID NO: 3)
5'-TACCGTTCGTATAGCATACATTATACGAAGTTAT-3'
```

```
Lox66:
                                          (SEQ ID NO: 4)
5'-ATAACTTCGTATAGCATACATTATACGAACGGTA-3' loxKMR:
                                          (SEQ ID NO: 5)
5'-ATAACTTCGTATAGCATACATTATACCTTGTTAT-3'
```

Subsequently, the targeting vector thus obtained is introduced into a plurality of ES cells (TT2 line) by an electroporation method for example to delete the Spink 3 (gene of interest) (step S13). TT2 line is an ES cell established using F1 obtained by mating a C57BL/6 female mouse and a CBA male mouse with each other, and is available from for example, Kumamoto University, Institute of Resource Development and Analysis. Here, GENE PULSER II (manufactured by Bio-Rad) can be used as an apparatus for performing the electroporation, and 800 V and 30 μF can be set as a condition for the electroporation. It is indisputable that the method and the condition for introducing the targeting vector into the ES cell are not limited to those exemplified herein.

After completing the electroporation, all of the ES cells were transferred to medium to which G418 that was neomycin had been added at a final concentration of 200 μg/ml, an cultured in an incubator at $CO_2$ concentration of 5% at temperature of 37° C. for several days. One having a composition shown in the following table can be used as the medium. Neomycin-resistant TT2 lines can be seeded in advance as feeder lines according to a standard method.

TABLE 1

| Ingredient | Concentration (/L) |
|---|---|
| DMEM (Sigma D5648) | 13.4 g |
| $NaHCO_3$ | 3.7 g |
| 2ME | 7 μl |
| Sodium phosphate | 0.11 g |

A mass of the ES cells grown after culturing for appropriate days is collected and separated into individual ES cells, which are then separately stored. It is examined by gene analysis whether objective homologous recombination occurs in these ES cells or not respectively. Those having the homologous recombination are used as Spink 3-deficient ES cells (step S14).

A blastocyst is generated using the Spink 3-deficient ES cells thus obtained by an aggregation method. The obtained blastocyst is grafted into uterus of a pseudopregnant C57BL/6J female mouse to produce a chimera mouse (F0) (step S15). The obtained chimera mouse and a C57BL/6J mouse are mated with each other to produce a Spink 3-heterozygously deficient mouse (F1) (step S16).

[Establishment of Mouse in which Predetermined Region on X Chromosome is Substituted with Spink 1] (Step S3)

As shown in FIG. 3, a Spink 1 minigene (substituted gene) is made as follows in order to establish this mouse (step S30).

Figure 4:
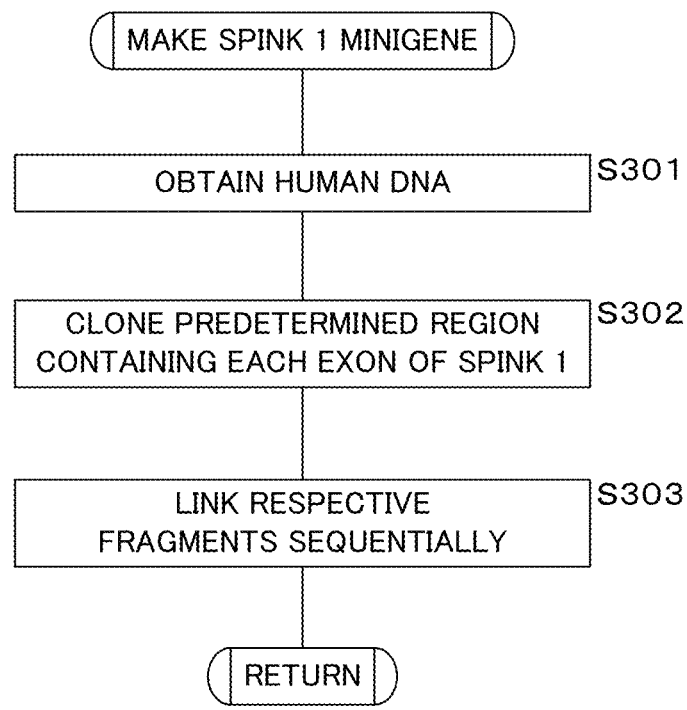
FIG. 4 is a flowchart illustrating one example of a procedure for making a Spink 1 minigene.

FIG. 4 is a flowchart illustrating the procedure for making the Spink 1 minigene. Blood is collected from a donor who has agreed, lymphocytes are separated from the blood, and human DNA is obtained from the obtained lymphocytes by performing the same manipulation as that in the aforementioned step S11 (step S301).

The Spink 1 gene is composed of four exons of exon 1 to exon 4. Each exon is cloned to include about 200 to 300 bp of intron on the 5' side and the 3' side, respectively (step S302). The design is performed not to clone the intron on the 5' side of the exon 1 and the intron on the 3' side of the exon 4. A size of the Spink 1 minigene is determined depending on a size of a region to be substituted on the X chromosome described later (Diap 2 gene in this embodiment).

Such a cloning can be performed using the following primers.

The primers for the exon 1 are as follows:

```
                                    (SEQ ID NO: 6)
SPINK1-ex1s1:    5'-TTCCAGTCCCAGGCTTCTGAA-3'

(SEQ ID NO: 7)
SPINK-in1a1:     5'-GGTCAGCCACATCAATAGAGG-3'
```

The primers for the exon 2 are as follows:

```
SPINK-na1s1Spe:
                                    (SEQ ID NO: 8)
5'-GCTCAGTGCCTGATTCATTTCCACTAGT-3'

SPINK1in2a2:
                                    (SEQ ID NO: 9)
5'-TCCACCCCAAATACTTGTCTAC-3'
```

The primers for the exon 3 are as follows:

```
SPINK1-in2s1Bam:
                                    (SEQ ID NO: 10)
5'-ACGGATCCATGTAAATCTAAATCTCACAAC-3'

SPINK1-in3a1Bam:
                                    (SEQ ID NO: 11)
5'-TAGGCTTGGATCCTACAAGTGACTTCTA-3'
```

The primers for the exon 4 are as follows:

```
SPINK1-in3s2:
                                    (SEQ ID NO: 12)
5'-GAGGCATCAGGAGCAAAAGCTTCA-3'

SPINK1-pAa2Hind:
                                    (SEQ ID NO: 13)
5'-GGTATAATCAAACAAAGCTTTGAGG-3'
```

Each fragment thus obtained was cloned into pGEM-T Easy Vector Systems (manufactured by Pr-omega).

Figure 5:
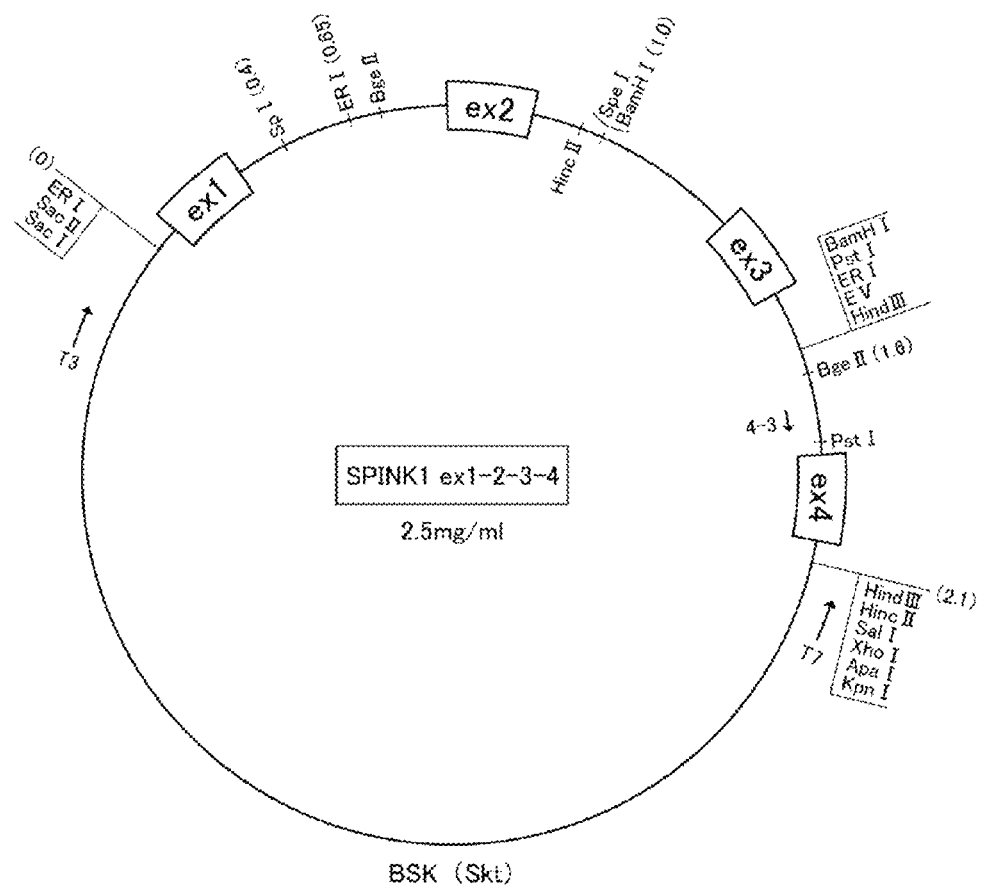
FIG. 5 is a map of pBluescript II SK(+) vector in which the Spink 1 minigene is cloned.

Subsequently in order to link respective fragments sequentially, the fragment containing the exon 1 is cut out from the corresponding cloning vector using restriction enzymes SacII and SpeI, and is bound to cloning sites of pBluescript II SK(+) vector. Then, the fragment containing the exon 2 is cut out from the corresponding cloning vector using the restriction enzyme SpeI, and is bound downstream of the fragment containing the exon 1 in the above vector. The same manipulation is performed sequentially for the fragment containing the exon 3 and the fragment containing the exon 4 to yield the Spink 1 minigene in which the fragment containing the exon 1 to the fragment containing the exon 4 have been sequentially linked as shown in FIG. 5 (step S303). The restriction enzyme BamHI can be used for the former cutting out and the restriction enzyme HindIII can be used for the latter cutting out.

Such a Spink 1 minigene can also be made by synthesizing its entire gene sequence. When the Spink 1 minigene is synthesized, the gene sequence is exemplified in SEQ ID NO:14. It is suitable to make the Spink 1 minigene by the synthesis because the Spink 1 minigene can be made without collecting the human blood.

Subsequently the Spink 1 minigene thus obtained is ligated to the downstream of CAG promoter (available from Kumamoto University, Institute of Resource Development and Analysis), and then a poly A sequence is bound to the 3' side of the Spink 1 minigene to yield a fragment containing (CAG promoter)-(Spink 1 minigene)-(poly A sequence), as shown in FIG. 3.

Figure 6:
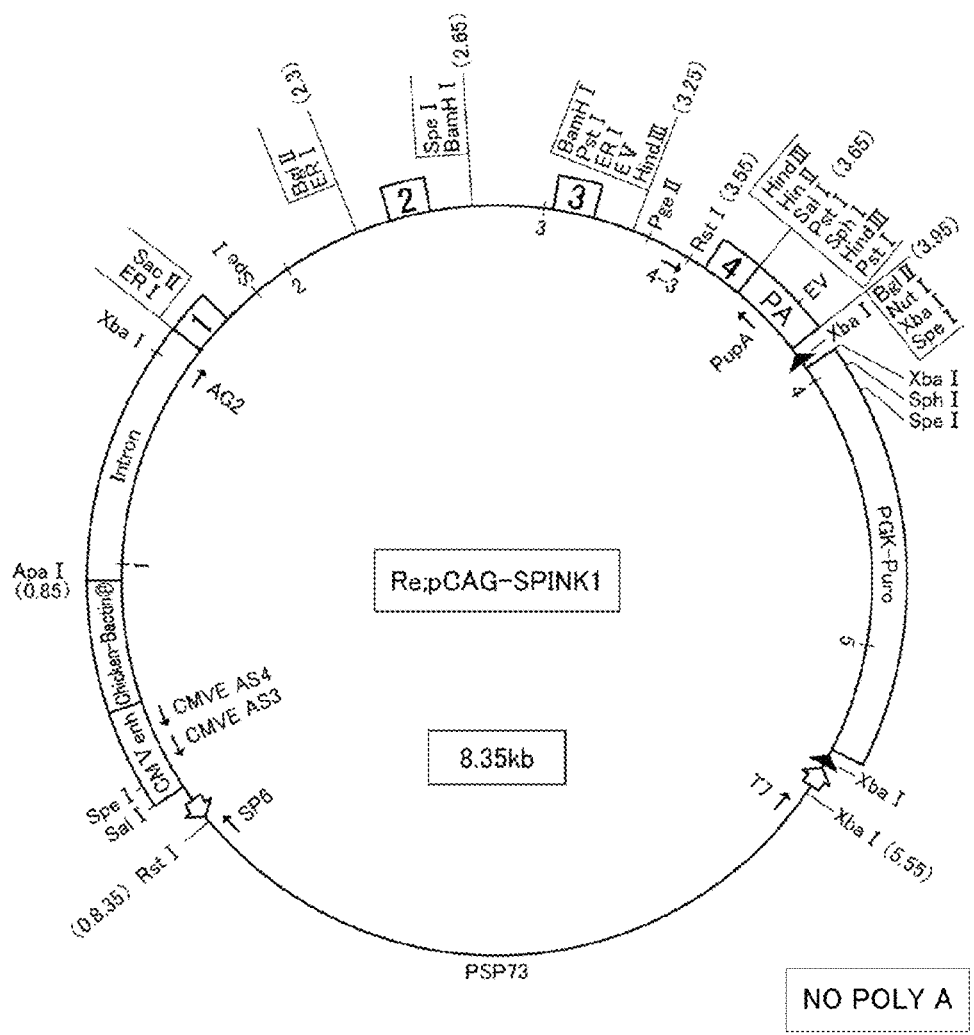
FIG. 6 is a map of a substitution vector.

A substitution vector including the mutant lox, the PGK promoter, PAC (puromycin N-acetyl transferase gene), poly A and the mutant lox in this order is made in advance. The fragment obtained as described above is inserted between the mutant lox and the PGK promoter in the substitution vector to make a substitution vector including (mutant lox)-(CAG)-(Spink 1 minigene)-(poly A sequence)-(PGK promoter)-(PAC)-(poly A)-(mutant lox) (step S32). The structure of this substitution vector is shown in FIG. 6.

Subsequently, an ES cell (second ES cell) in which the Diap 2 gene in a C57BL/6J mouse is heterozygously deficient and a Cre expression vector (available from Kumamoto University, Institute of Resource Development and Analysis) are prepared in advance. This ES cell was domestically deposited to Incorporated Administrative Agency, National institute of Technology and Evaluation (NITE), Patent Microorganisms Depositary (NPMD) (2-5-8 Kazusa Kamatari, Kisarazu-shi, Chiba Prefecture, Japan, 292-0818) on Dec. 1, 2011 (original deposit date), and an accession number of NITE P-1172 has been given. Further, this ES cell was transferred to the international depositary of the Patent Microorganisms Depositary on May 30, 2012 (transfer date), and the accession number of NITE BP-1172 has been given on Jun. 11, 2012.

Scientific natures of this ES cell are as follows.

That is, this ES cell (second ES cell) is obtained by making a TT2 ES cell made from an F1 blastocyst of a B6 mouse and a CBA mouse free from feeder cells, introducing a trap vector pU-21B into the cell and further making the cell resistant to an antibiotic (G418). The trap vector is inserted into a diaphanous homolog 2 (Drosophila) (Diap 2) gene, and a reporter gene 6-geo is expressed by an activity of a Diap 2 gene promoter.

This Diap 2 gene is located on the X chromosome. As described above, the Diap 2 gene is deleted by introducing the trap vector pU-21B (available from Kumamoto University, Institute of Resource Development and Analysis) into the Diap 2 gene region on one of the paired X chromosomes in the present ES cell. It has been confirmed that the mouse in which the Diap 2 gene is deficient is normal.

Figure 15:
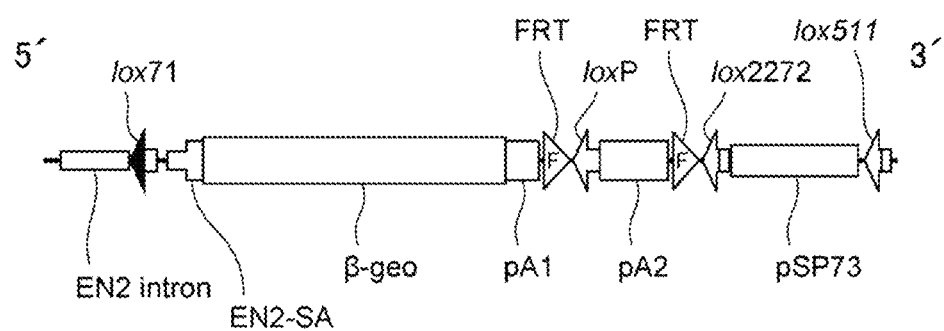
FIG. 15 a schematic view illustrating a structure of pU-21B.

FIG. 15 is a schematic view illustrating the structure of pU-21B. FIG. 16 is a schematic view illustrating the structure of pU-21B after being introduced into the Diap 2 gene region. This pU-21B is introduced into a location that is present in an intron flanking to a downstream side of the 29th exon of the Diap 2 gene and is 5.3 kb downstream from the 29th exon in this ES cell.

As shown in FIG. 15, pU-21B is composed of (EN2 intron)-(lox 71)-(EN2-SA)-(β-geo)-(pA1)-(FRT)-(loxP)-(pA2)-(FRT)-(lox2272)-(pSP73)-(lox511) sequentially from the 5' side, and the region between lox71 and loxP can be substituted with another gene. lox71 and loxP are added to the 5' side and 3' side, respectively of another gene to be substituted.

Meanwhile, the structure of pU-21B after being introduced into the Diap 2 gene region was analyzed, and a region of 1321 bp on the 5' side and a region of 1 kb or more on the 3' side were deleted as shown in FIG. 16. That is, the region of the EN2 intron was partially deleted on the 5' side, and the region of lox511 was entirely deleted and the region of pSp73 was partially deleted on the 3' side.

The case in which the gene of interest is deleted to be substitutable with another gene by introducing pU-21B into the Diap 2 gene on one X chromosome has been described as the second ES cell in this embodiment, but the present invention is not limited thereto. It is indisputable that another trap vector may be used. In such a case, the location of the trap vector to be introduced into the Diap 2 gene may be different from that of aforementioned pU-21B according to the structure of the trap vector to be used. Various constitutions of substitutable genes in the trap vector can be constructed.

The above substitution vector and the Cre expression vector are introduced into a plurality of Diap 2-heterozygously deficient ES cells (second ES cells) by the electroporation method (step S33). An introduction condition of 400 V and 125 μF can be set. This can generate a substituted body in which the aforementioned particular region in the Diap 2 gene-deficient region on the X chromosome has been substituted with (CAG)-(Spink 1 minigene)-(poly A sequence)-(PGK promoter)-(PAC).

After completing the electroporation, all of the ES cells were transferred to medium to which puromycin had been added at a concentration of 2 μg/ml and cultured in the incubator at $CO_2$ concentration of 5% at 37° C. for several days. Puromycin-resistant ES cells can be seeded in advance as the feeder cells according to the standard method.

A mass of the ES cells grown after culturing for appropriate days is collected and separated into individual ES cells, which are then separately stored. It is examined by the gene analysis whether the objective substitution occurs in these ES cells or not respectively. Those having the substitution are used as substituted ES cells (step S34).

A blastocyst is generated by the aggregation method using the substituted ES cells thus obtained, and the obtained blastocyst is grafted into the uterus of a pseudopregnant C57BL/6J female mouse to produce an individual, thereby producing a mouse (second individual) in which the predetermined region on the X chromosome has been substituted with Spink 1, i.e., Spink 1 has been knocked in the X chromosome (step S35).

[Establishment of Model Animal]

The Spink 3-heterozygously deficient mouse and the Spink 1-knock-in mouse in which Spink 1 has been knocked in the X chromosome are obtained as described above. Then as shown in FIG. 1, both the mice are mated with each other to establish a Spink $3^{+/-}$YXCAG-SP1 (male) and Spink $3^{+/-}$XCAG-SP1/Wild (female).

Then, these mice are mated with each other to establish a model animal of Spink $3^{-/-}$XCAG-SP1/Wild (step S5).

Here, the gene dosage compensation in the mammalian animal is accomplished by inactivating one of the two X chromosomes in the female, and such a phenomenon is referred to as "X chromosome inactivation". It is random that which of the two X chromosomes may be inactivated. Thus, those having Spink $3^{-/-}$ XCAG-SP1 in which Spink 3 is deficient while the deficiency is rescued by Spink 1 on the X chromosome and those having Spink $3^{-/-}$ XWild in which Spink 3 is deficient and such a rescue is not made are randomly present in cells that compose pancreas of the model mouse established as described above. Thereby, the model mouse develops chronic pancreatitis as described later.

Subsequently, the results of pathological analysis performed for the model mouse of Spink $3^{-/-}$XCAG-SP1/Wild thus obtained will be described.

Figure 7:
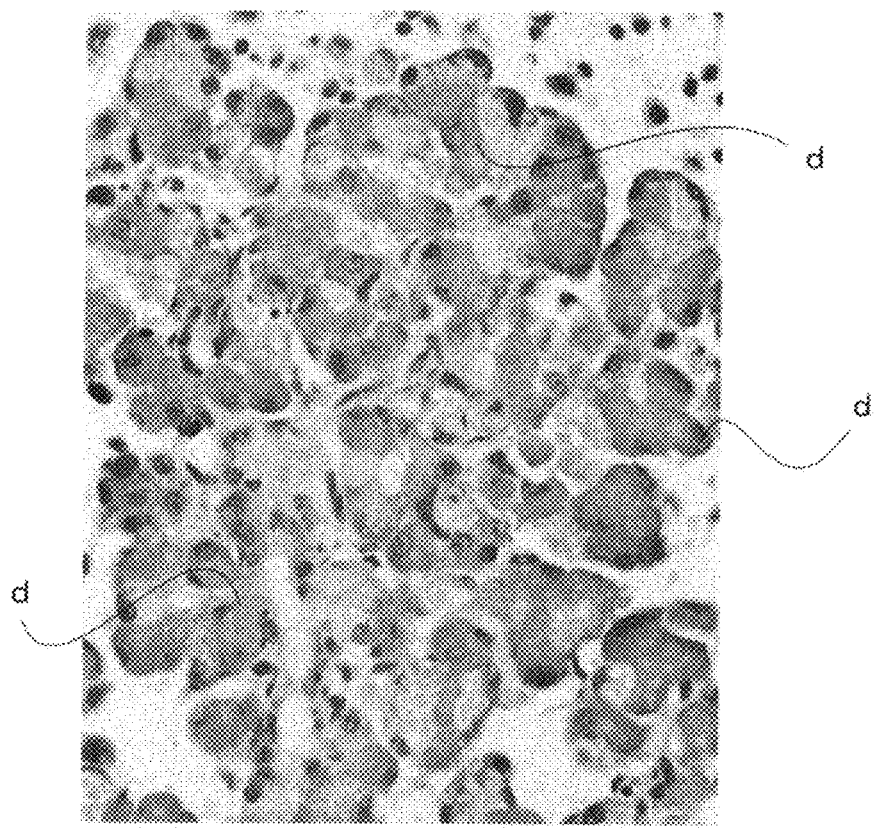
FIG. 7 is a microscopic image view of a pancreatic slice from a model mouse produced by the method of the present invention.
Figure 12A:
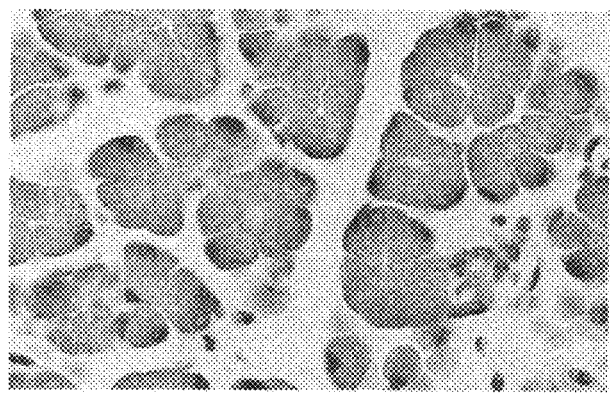
FIGS. 12A and 12B are microscopic image views of a pancreatic slice from a conventional model mouse.
Figure 12B:
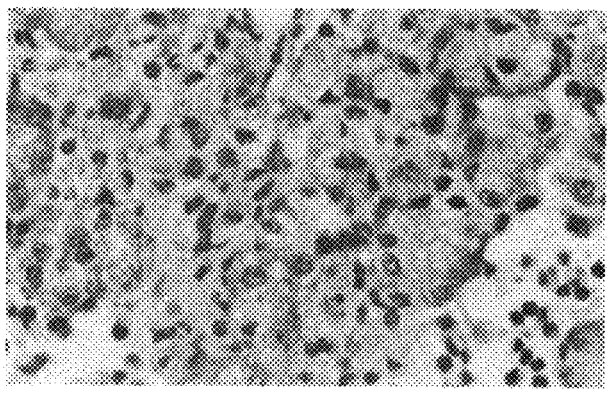

FIG. 7 is a microscopic image view of a pancreatic slice from the model mouse of Spink $3^{-/-}$XCAG-SP1/Wild produced by the method of the present invention. FIG. 12A is a microscopic image view of a pancreatic slice from the Spink 3-heterozygously deficient (Spink $3^{+/-}$) mouse, and FIG. 12B is a microscopic image view of a pancreatic slice from the Spink 3-homozygously deficient (Spink $3^{-/-}$) mouse. All of these slices are obtained from the mice 0.5 day after birth, and stained with HE (hematoxylin and eosin).

As shown in FIG. 12A, pancreatic parenchyma (acinar cells) is normal in the pancreas of the Spink 3-heterozygously deficient mouse, whereas as shown in FIG. 12B, most acinar cells are dropped off in the pancreas of the Spink 3-homozygously deficient (Spink $3^{-/-}$) mouse.

On the contrary, as is evident from FIG. 7, the acinar cells are observed while dropping off acinar cells are also observed as indicated in the figure(d) in the pancreas from the model mouse according to the present invention. That is, the acinar cells having Spink $3^{-/-}$XCAG-SP1 in which Spink 3 is deficient whereas the deficiency is rescued by Spink 1 on the X chromosome remain in the pancreas, and the acinar cells having Spink $3^{-/-}$/XWild in which Spink 3 is deficient and such a rescue is not made are dropped off in the pancreas.

Meanwhile, FIG. 8 is a microscopic image view of a pancreatic slice from a model mouse aged 8 weeks of Spink $3^{-/-}$XCAG-SP1/Wild produced by the method of the present invention. FIG. 13 is a microscopic image view of a pancreatic slice from a Spink 3-heterozygously deficient (Spink $3^{+/-}$) mouse aged 8 weeks. Both the slices were stained with HE.

As is evident from FIG. 13, enlargement of a pancreatic duct was not observed in the pancreas from the Spink 3-heterozygously deficient mouse. On the contrary, as is evident from FIG. 8, the clear enlargement of the pancreatic duct was observed in the pancreas from the model mouse according to the present invention.

Further, the pancreatic slices shown in FIGS. 8 and 13 were stained with Azan that could stain collagenous fibers and muscle fibers distinctively. The results are shown in FIGS. 9 and 14.

Comparing FIG. 9 with FIG. 14, tissue surrounding the pancreatic duct did not become so fibrotic in the Spink 3-heterozygously deficient mouse, but the tissue surrounding the pancreatic duct became excessively fibrotic in the model mouse according to the present invention.

As described above, the model mouse according to the present invention was alive for 8 weeks or more, while the dropping off of pancreatic parenchyma (acinar cells) and the enlarged pancreatic duct as well as excessive fibrosis in the tissue surrounding them were observed in the pancreas of the model mouse, which were closely resemble to pathological features of human chronic pancreatitis.

Subsequently, the results of examining the gene expression in the cells that compose the pancreas of the model mouse according to the present invention will be described.

Figure 10:
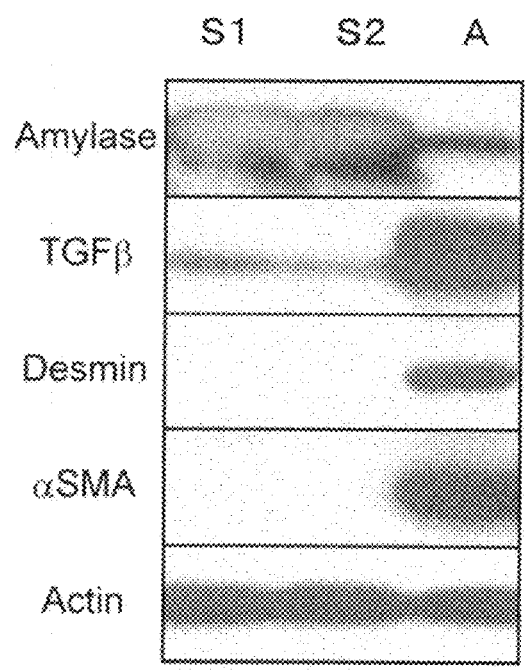
FIG. 10 is an image view showing a result of examining the presence or absence of expression of various markers by a western blotting method.

FIGS. 10 and 11 are image views showing the results of examining the presence or absence of the expression of various markers by a western blotting method. In the figures, the pancreas from the model mouse according to the present invention was used in the case (A), the pancreas from the Spink 3-heterozygously deficient (Spink $3^{+/-}$) mouse was used in the case (S1), and the pancreas from the mouse of Spink $3^{-/-}$XCAG-SP1/CAG-SP1 was used in the case (S2). The pancreas from the mouse aged 8 weeks was used in all of the cases. The mouse of Spink $3^{-/-}$XCAG-SP1/CAG-SP1 was derived from the mating of Spink 3$^{+/-}$YXCAG-SP1 with Spink 3$^{+/-}$XCAG-SP1/Wild as described above, and the produced one was used.

As is evident from FIGS. 10 and 11, TGFβ that is the marker of a substance promoting the fibrosis of the tissue, Desmin and αSMA that are the markers of pancreatic stellate cells, and Her2 and Ras that are the markers for carcinogenesis and promotion of tumor growth were expressed at high levels in the model mouse according to the present invention. On the contrary, these markers were scarcely expressed in the Spink 3-heterozygously deficient mouse and the mouse of Spink 3$^{-/-}$XCAG-SP1/CAG-SP1 because these mice were normal.

Meanwhile, amylase that is a digestive enzyme was expressed at high levels in the Spink 3-heterozygously deficient mouse and the mouse of Spink 3$^{-/-}$XCAG-SP1/CAG-SP1, but was scarcely expressed in the model mouse according to the present invention.

The method for producing the model mouse that develops chronic pancreatitis has been described in this embodiment, but the present invention is not limited thereto, and can be applied to the production of a model mouse that develops diabetes, pancreatic cancer, or the like. The present invention can also be applied to purification of pancreatic stellate cells in a large amount, fibrosis of the organs, and the like, other than the disease. Meanwhile, the animal to be subjected is not limited to mice, and the present invention can be applied to other non-human mammalian animals such as rats and rabbits.

The case in which the fragment containing the homologous gene is introduced into one of the paired X chromosomes has been described in this embodiment, but the present invention is not limited thereto, and the homologous gene may be introduced into both the paired X chromosomes. In this case, a fragment containing the homologous gene and a promoter and a fragment containing the homologous gene but containing no promoter are prepared. Both the fragments are introduced into an ES cell constituted so that a predetermined region of both the paired X chromosomes can be substituted, thereby obtaining the ES cell in which the former fragment is introduced into one of the paired X chromosomes and the latter fragment is introduced into the other of the paired X chromosomes. That is, although the homologous gene is introduced into both the paired X chromosomes, the homologous gene introduced into one X chromosome is expressed whereas the homologous gene introduced into the other X chromosome is not expressed.

This yields a model animal in which cells in which the gene of interest is deficient but the deficiency is rescued by the homologous gene on the X chromosome and cells in which the gene of interest is deficient and such a rescue is not made are randomly present in the target portion because one of the X chromosomes is inactivated as described above. Such a model animal has the desired lifetime and induces the predetermined biological reaction, like above. In this regard however, the aforementioned method of introducing the fragment containing the homologous gene into one of the paired X chromosomes is more efficient in production of the model animal than such a method.

By the way, as is evident from the above description, the following inventions are further brought from this embodiment.

(1) A method for producing a model animal, comprising:
when producing a model animal in which a gene of interest is deficient using an ES cell from a non-human mammalian animal,
obtaining a first individual in which the gene of interest is heterozygously deficient;
performing
a step of making a fragment containing a homologous gene of the gene of interest,
a step of using a second ES cell constituted so that a predetermined region in a Diap 2 gene on one of paired X chromosomes of the non-human mammalian animal can be substituted to generate a substituted ES cell in which the predetermined region is substituted with the fragment by introducing the fragment into the second ES cell, and
a step of producing a second individual using the obtained substituted ES cell; and
producing a model animal by mating the first individual and the second individual with each other.

(2) The method for producing the model animal according to (1), wherein a mouse is used as the non-human mammalian animal and an ES cell (NITE BP-1172) is used as the second ES cell.

(3) The method for producing the model animal according to (2), wherein the gene of interest is a Spink 3 gene and the homologous gene is a Spink 1 gene.

The method for producing the model animal according to (1) is characterized in that when a model animal in which a gene of interest is deficient is produced using an ES cell from a non-human mammalian animal, a first individual in which the gene of interest is heterozygously deficient is obtained and is characterized by performing a step of making a fragment containing a homologous gene of the gene of interest, a step of using a second ES cell constituted so that a predetermined region in a Diap 2 gene of one of paired X chromosomes of the non-human mammalian animal can be substituted to generate a substituted ES cell in which the predetermined region is substituted with the fragment by introducing the fragment into the second ES cell and a step of producing a second individual using the obtained substituted ES cell; and by producing a model animal by mating the first individual and the second individual with each other.

In the method for producing the model animal of the present invention, the first individual in which the gene of interest is heterozygously deficient is obtained by the standard method.

On the other hand, the fragment containing the homologous gene that has homology to the aforementioned gene of interest is made. In such a step, the homologous gene may be cloned, or the gene sequence designed to contain each exon may be synthesized.

Then, by using the second ES cell consisted so that the predetermined region in the Diap 2 gene on one of the paired X chromosomes in the subject animal can be substituted, and the substituted ES cell in which the predetermined region has been substituted with the fragment by introducing the fragment into the second ES cell is generated. The Diap 2 gene is located on the X chromosome, and it has been confirmed that the mouse in which the Diap 2 gene is deficient is normal. The second ES cell constituted so that the predetermined region on the X chromosome can be substituted by introducing an appropriate vector into this Diap 2 gene is used, and the above fragment is introduced together with an expression vector such as Cre expression vector into the second ES cell, thereby generating the substituted ES cell in which the predetermined region has been substituted with the above fragment.

Subsequently, the obtained substituted ES cell is treated appropriately, then transferred into the pseudopregnant animal to produce the individual, and the second individual in which the predetermined region on the X chromosome has been substituted with the homologous gene is selected from the obtained individuals.

And, the first individual and the second individual are mated with each other to produce a female model animal in which the gene of interest has been homozygously deficient and the homologous gene has been introduced into one of the paired X chromosomes.

Here, the gene dosage compensation in the mammalian animal is accomplished by inactivating one of two X chromosomes in the female, and such a phenomenon is referred to as the "X chromosome inactivation". Any one of the two X chromosomes is randomly inactivated. Thus, in the model animal produced as above, cells in which the gene of interest is deficient but the deficiency is rescued by the homologous gene on the X chromosome and cells in which the gene of interest is deficient and such a rescue is not made randomly compose the target part. Such a model animal has the desired lifetime and induces the predetermined biological reaction.

Also as described above, the subject animal in which the Diap 2 gene on the X chromosome is deficient is normal. Thus, when the ES cell in which the Diap 2 gene on the X chromosome is deficient is used as the second ES cell, the predetermined biological reaction can be induced without giving the harmful effect to the obtained model animal.

The method for producing the model animal according to (2) is characterized by using the mouse as the animal and using the ES cell (NITE BP-1172) as the second ES cell.

In the method for producing the model animal of the present invention, the mouse is used as the animal and the ES cell (NITE BP-1172) is used as the second ES cell. This second ES cell was domestically deposited to Incorporated Administrative Agency, National Institute of Technology and Evaluation (NITE), Patent Microorganisms Depositary (NPMD) (2-5-8 Kazusa Kamatari, Kisarazu-shi, Chiba Prefecture, Japan, 292-0818) on Dec. 1, 2011 (original deposit date), and an accession number of NITE BP-1172 has been given. Further, this ES cell was transferred to the international depositary of the Patent Microorganisms Depositary on May 30, 2012 (transfer date), and the accession number of NITE BP-1172 has been given on Jun. 11, 2012.

This second ES cell (NITE BP-1172) is constructed by introducing the trap vector pU-21B into the aforementioned Diap 2 gene, and the predetermined region of the trap vector pU-21B can be substituted with another fragment. Therefore, the homologous gene can be introduced into the Diap 2 gene by substituting this substitutable region with the homologous gene. Meanwhile, the mouse in which the Diap 2 gene is deficient is normal as described above. Thus, when the ES cell (NITE BP-1172) is used as the second ES cell, the predetermined biological reaction can be induced without giving the harmful effect to the obtained model mouse.

The method for producing the model animal according to (3) is characterized in that the gene of interest is the Spink 3 gene and the homologous gene is the Spink 1 gene.

In the method for producing the model animal of the present invention, the gene of interest is the Spink 3 gene and the homologous gene is the Spink 1 gene. Thus, the observations characteristic for human chronic pancreatitis can be observed in the obtained model mouse.

As described above, the present invention can be applied to the production of the model animal that develops chronic pancreatitis, diabetes, pancreatic cancer, or the like. The present invention can also be applied to the purification of pancreatic stellate cells in a large amount, fibrosis of the organs, and the like, other than the disease.

It is to be noted that the disclosed embodiment is illustrative and not restrictive in all aspects. The scope of the present invention is defined by the appended claims rather than by the description preceding them, and all changes that fall within metes and bounds of the claims, or equivalence of such metes and bounds thereof are therefore intended to be embraced by the claims.

The invention claimed is:

1. A method for producing a mosaic, transgenic mouse whose genome comprises a heterozygous deletion of a gene of interest and mosaic expression of a homologue of the gene of interest comprising:
   a) deleting the gene of interest from the genome of a mouse ES cell;
   b) producing a first mouse whose genome comprises a heterozygous deletion of the gene of interest using the ES cell;
   c) generating a nucleic acid comprising a gene homologous to the gene of interest;
   d) introducing the nucleic acid into the Diap2 locus of the X chromosome of a second mouse ES cell that is constituted such that the Diap2 locus can be substituted with the nucleic acid;
   e) producing a second mouse using the ES cell; and
   f) producing a mosaic, transgenic mouse by mating the first and second mice,
   wherein the nucleic acid comprising a gene homologous to the gene of interest is silenced in a subset of cells of the mosaic mouse due to X-chromosome inactivation and is active in the remaining cells where the X-chromosome comprising the nucleic acid is not inactivated.

2. The method for producing the model mouse according to claim 1, wherein an ES cell (NITE BP-1172) is used as the second ES cell.

3. The method for producing the model mouse according to claim 1, wherein the gene of interest is a Spink 3 gene and the homologous gene is Spink 1 gene.

* * * * *

SEQUENCE LISTING

```
<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: primer of PCR

<400> SEQUENCE: 1
tacgtctccg gtcttctt                                                     18

<210> SEQ ID NO 2
<211> LENGTH: 21
<212> TYPE: DNA
<213> ORGANISM: Artificial Sequence
<220> FEATURE:
<223> OTHER INFORMATION: primer of PCR

<400> SEQUENCE: 2
gatccggaac ccttaatata a                                                 21

<210> SEQ ID NO 3
<211> LENGTH: 34
<212> TYPE: DNA
<213> ORGANISM: Artificial Sequence
<220> FEATURE:
```

<223> OTHER INFORMATION: primer of PCR

<400> SEQUENCE: 3
taccgttcgt atagcataca ttatacgaag ttat                                    34

<210> SEQ ID NO 4
<211> LENGTH: 34
<212> TYPE: DNA
<213> ORGANISM: Artificial Sequence
<220> FEATURE:
<223> OTHER INFORMATION: primer of PCR

<400> SEQUENCE: 4
ataacttcgt atagcataca ttatacgaac ggta                                    34

<210> SEQ ID NO 5
<211> LENGTH: 34
<212> TYPE: DNA
<213> ORGANISM: Artificial Sequence
<220> FEATURE:
<223> OTHER INFORMATION: primer of PCR

<400> SEQUENCE: 5
ataacttcgt atagcataca ttataccttg ttat                                    34

<210> SEQ ID NO 6
<211> LENGTH: 21
<212> TYPE: DNA
<213> ORGANISM: Artificial Sequence
<220> FEATURE:
<223> OTHER INFORMATION: primer of PCR

<400> SEQUENCE: 6
ttccagtccc aggcttctga a                                                  21

<210> SEQ ID NO 7
<211> LENGTH: 21
<212> TYPE: DNA
<213> ORGANISM: Artificial Sequence
<220> FEATURE:
<223> OTHER INFORMATION: primer of PCR

<400> SEQUENCE: 7
ggtcagccac atcaatagag g                                                  21

<210> SEQ ID NO 8
<211> LENGTH: 28
<212> TYPE: DNA
<213> ORGANISM: Artificial Sequence
<220> FEATURE:
<223> OTHER INFORMATION: primer of PCR

<400> SEQUENCE: 8
gctcagtgcc tgattcattt ccactagt                                           28

<210> SEQ ID NO 9
<211> LENGTH: 22
<212> TYPE: DNA
<213> ORGANISM: Artificial Sequence
<220> FEATURE:
<223> OTHER INFORMATION: primer of PCR

<400> SEQUENCE: 9
tccaccccaa atacttgtct ac                                                 22

```
<210> SEQ ID NO 10
<211> LENGTH: 30
<212> TYPE: DNA
<213> ORGANISM: Artificial Sequence
<220> FEATURE:
<223> OTHER INFORMATION: primer of PCR

<400> SEQUENCE: 10
acggatccat gtaaatctaa atctcacaac                                          30

<210> SEQ ID NO 11
<211> LENGTH: 28
<212> TYPE: DNA
<213> ORGANISM: Artificial Sequence
<220> FEATURE:
<223> OTHER INFORMATION: primer of PCR

<400> SEQUENCE: 11
taggcttgga tcctacaagt gacttcta                                            28

<210> SEQ ID NO 12
<211> LENGTH: 24
<212> TYPE: DNA
<213> ORGANISM: Artificial Sequence
<220> FEATURE:
<223> OTHER INFORMATION: primer of PCR

<400> SEQUENCE: 12
gaggcatcag gagcaaaagc ttca                                                24

<210> SEQ ID NO 13
<211> LENGTH: 25
<212> TYPE: DNA
<213> ORGANISM: Artificial Sequence
<220> FEATURE:
<223> OTHER INFORMATION: primer of PCR

<400> SEQUENCE: 13
ggtataatca aacaaagctt tgagg                                               25

<210> SEQ ID NO 14
<211> LENGTH: 2051
<212> TYPE: DNA
<213> ORGANISM: Homo sapiens

<400> SEQUENCE: 14
ttccagtccc aggcttctga agagacgtgg taagtgcggt gcagttttca actgacctct         60
ggacgcagaa cttcagccat gaaggtaaca ggcatctttc ttctcagtgc cttgccctg         120 ttgagtctat ctggtaagtg ttgcatattt tcaaattta ataaaactg ttttgacctg          180 ttgctttgtg aagcacatta tcttctagac ttttgatgta gtctagtctt cgagagatgt        240
tttggaccta atgagatgaa ataaaatcaa caggtaagaa ttattttta agaggaattt         300 ttaacctact ataaggaaaa caattctact agtgattgct cagtgcctga ttcatttcca        360
gcagtaagtg cataatttct gttttcaagg aaatagatca acttcctaaa acatcaaatc        420
gagatacttt ggtcataatc aaagttttac tcaaactttt taaggttttg ccaaggaagg       480
ggtacaggaa aatcagccag atacttttgg aagattagag aaatcagaaa gggtggggaa        540
tgaaagagcc tagtaaagaa gtcacagtct gcaatgaaag cagagaattc tgatgaagaa        600
tagatctgac ttctttcatt taggacccaa cttaccatat ctgatttatt tctaggtaac        660
actggagctg actccctggg aagagaggta aagagatatt tgtaatttct tatttctcag        720
```

```
actggaacag tttgatccaa caaaaatgca gccttgctgt cacctttcag tttagcctga    780
agttaagagg agtatgaatg ctagggaggg ttaacgtgag aaatgcaaat ggtagtagta    840
gttccaaccc acaggcgtat attgaaggac aatttcactg atgtataagc aagttccata    900
tagtcctaca gtgcttgctg tgaagggggtt tttatataga ctagtggatc catgtaaatc    960
tcacaacaac actatgagat aggtgggaaa tggcaatatc atcactgttt tgcagatgaa   1020
ctgactgagt ttcagaaggg ccataggact tactaatgtc acacagctta gaaatagcag   1080
aggcatgact taaaacaagg ttttctgtct ccagacagta ggttatttct cttacaacac   1140
acagtatcat tctcccaatc acagttattc cccagagaaa taaaaccatt tcagagattt   1200
tgctatgaac tcaagaatgg agaataatgg gaaatgattc tgtttaattc catttttagg   1260
ccaaatgtta caatgaactt aatggatgca ccaagatata tgaccctgtc tgtgggactg   1320
atggaaatac ttatcccaat gaatgcgtgt tatgttttga aaatcggtga gtacaaactt   1380
gagtttcttt taaactatat attttaagtt agttatcttc aagtgtactg ataatatgaa   1440
tctcaccccg agaaaagcaa actatttact ttttccaaaa acagttatct ctttcttatt   1500 ctcccttttta tatatttagc attaaatatt attttttaga agtcacttgt aggatccccc   1560
gggctgcagg aattcgatat caagcttcaa caatagtttt gagtttaatt tcagggttc   1620 actgtaacac cccacgagat ctgtaaaaac tgtaaggaca gatatttttc ctttctgttg   1680
tatccttagt gtattcaaca gtaatcaata aatatttgat gaattaatga ctaagtgaat   1740
gtataaatga atgaaagaca gagaaaagat tataaatctc aaacctctcc aactttaaat   1800
gaagctgtta tttttcccccc tgtttttctc ccatagtcac tttttcatca gtgaagttta   1860
agctgatata tttttttttaa tctctactgc aggaaacgcc agacttctat cctcattcaa   1920
aaatctgggc cttgctgaga accaaggttt tgaaatccca tcaggtcacc gcgaggcctg   1980
actggcctta ttgttgaata aatgtatctg aatatcccct gttgtttcca tttgcttttt   2040
cctcaaaggt a                                                        2051
```